United States Patent [19]

Sell et al.

[11] Patent Number: 4,567,149
[45] Date of Patent: * Jan. 28, 1986

[54] BINDING ASSAY SYSTEM AND METHOD OF MAKING AND USING SAME

[75] Inventors: William J. Sell, San Francisco; David H. Riege, Newark; Vincent A. Marinkovich, Palo Alto, all of Calif.

[73] Assignee: Mast Immunosystems, Ltd., Mountain View, Calif.

[*] Notice: The portion of the term of this patent subsequent to Jul. 10, 2001 has been disclaimed.

[21] Appl. No.: 476,367

[22] Filed: Mar. 17, 1983

[51] Int. Cl.[4] .................. G01N 33/053; G01N 23/06; C12M 1/00; C01N 33/544

[52] U.S. Cl. .................................... 436/513; 422/61; 422/68; 422/71; 435/287; 436/530

[58] Field of Search ............. 435/4, 7, 287, 291-293, 435/300, 301; 436/513, 530, 804, 805, 807-809; 424/1.5, 12, 20; 422/56-58, 61, 68, 71

[56] References Cited

U.S. PATENT DOCUMENTS

| | | | |
|---|---|---|---|
| 3,925,116 | 12/1975 | Blume | 435/301 |
| 4,230,757 | 10/1980 | Toner | 422/56 |
| 4,284,725 | 8/1981 | Fennel, III et al. | 435/5 |
| 4,459,360 | 7/1984 | Marinkovich | 436/530 |

Primary Examiner—Robert J. Warden
Assistant Examiner—Cynthia Lee Foulke
Attorney, Agent, or Firm—Fulwider, Patton, Rieber, Lee & Utecht

[57] ABSTRACT

Method and apparatus for use in the diagnostic analysis of a liquid specimen through binding assays. The apparatus includes a rigid body having an elongated, shallow well formed in it, with a plurality of elongated strips, preferably in the form of cotton threads, stretched across the well in spaced relationship and generally perpendicular to the well's longitudinal axis. Each thread is coated with a separate binding conjugate such as an antigen or allergen. A cover plate that includes a thin plastic layer and an overlaying thin metallic layer covers the well to form an enclosed chamber having a specific volume. The metallic layer includes a separate elongated aperture in alignment with each coated thread. A liquid specimen is introduced into the chamber through one of two ports, for incubation with the coated threads, after which the specimen is removed and the reaction that occurred on each thread is determined.

17 Claims, 5 Drawing Figures

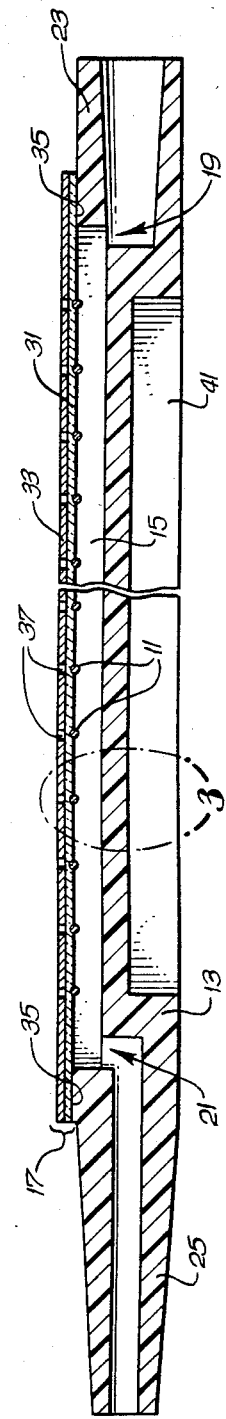
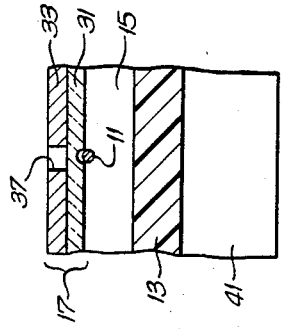
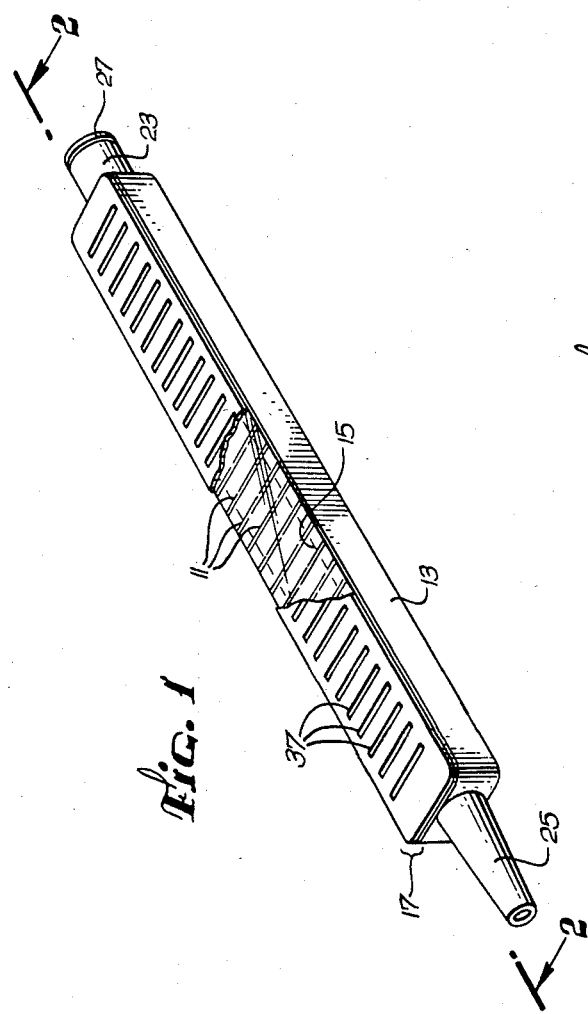

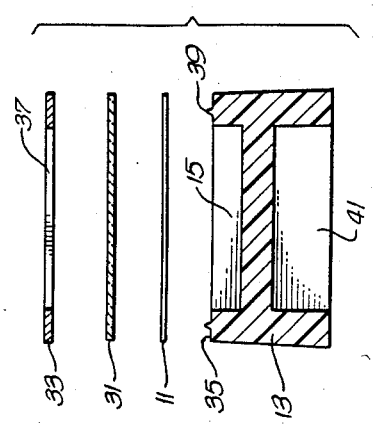
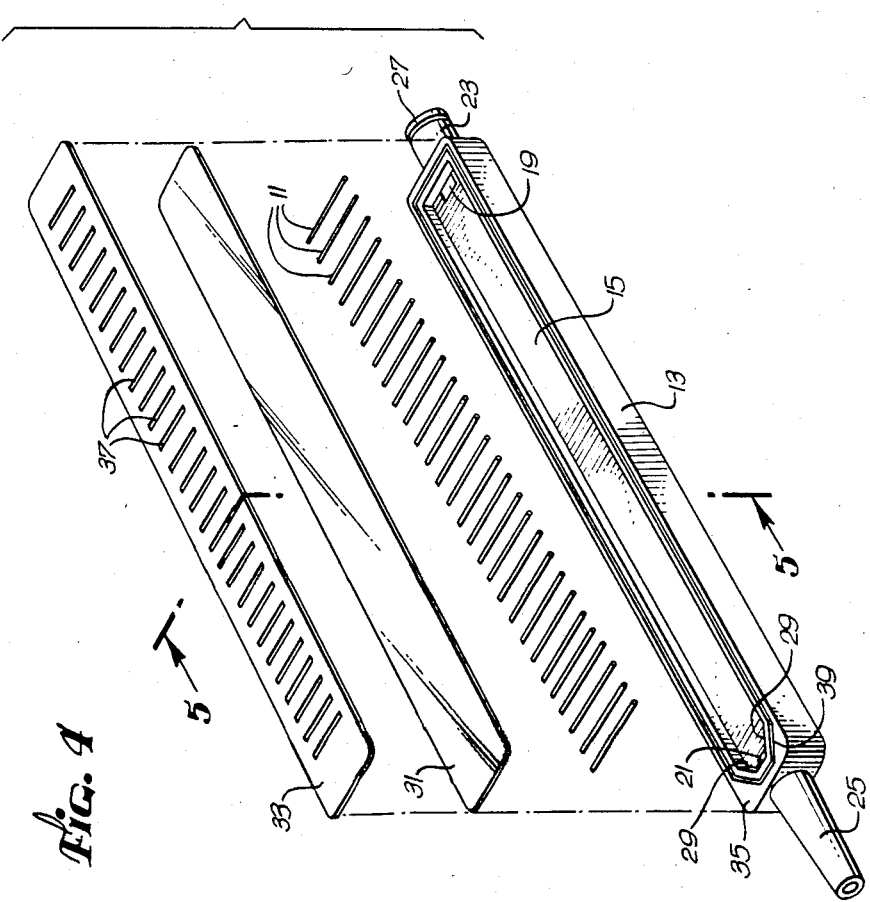

BINDING ASSAY SYSTEM AND METHOD OF MAKING AND USING SAME

BACKGROUND OF THE INVENTION

This invention relates generally to devices for use in the diagnostic analysis of liquid specimens through binding assays, and, more particularly, to devices of this type for use in multiple simultaneous testing of such liquid specimens.

One device of this particular type is disclosed in a copending and commonly-assigned application for U.S. patent Ser. No. 308,935, filed on Oct. 5, 1981, in the name of Vincent A. Marinkovich now issued as U.S. Pat. No. 4,459,360, entitled "Multiple-Component Binding Assay System and Method of Making and Using It." The application discloses a diagnostic kit that includes a support and a plurality of cotton filaments secured to the support in spaced relationship, for simultaneous contact with a liquid test sample. Each filament is coated with a unique binding assay component, such as an allergen, that is covalently bound through cyanogen halide induced linkages.

In use, the support and filaments are incubated with a liquid specimen, and the amount of multiple biological agents interacting with the binding assay components coated on the filaments is determined. When screening for the presence of multiple allergen-specific IgE class antibodies in a liquid sample, the device is incubated with the test sample and then, after washing, incubated with a solution containing labeled antibodies against the IgE class antibodies that have bound to the filaments. The filaments are then analyzed to determine the presence of the labeled antibodies. If the labeled antibodies are labeled with a radioactive tracer, such as $^{125}I$, this analysis can be accomplished using a gamma counter. Alternatively, the analysis can be accomplished by placing the filaments adjacent to photographic film for exposure and by then measuring the degree of exposure.

Although the device described above has performed well in allergy screening, it is not believed to be entirely satisfactory. One reason for this is that the allergen-coated filaments are exposed during handling, which might have an effect on the outcome of the testing. In addition, there is no guarantee that each device will always be used with a specific amount of the liquid specimen, which might affect the repeatability of the testing. Moreover, when used with radioactively-labeled antibodies, such as $^{125}I$, the filaments themselves can become radioactive, thereby making subsequent handling of the devices somewhat hazardous. Still another drawback to the device described above is that a strong reaction on one of the filaments can mask or otherwise interfere with the measuring of the reactions on adjacent filaments.

It should be appreciated from the foregoing that there still is a need for a device for use in the diagnostic analysis of liquid specimens using binding assays, that can be used for multiple simultaneous testing of the sample and that is relatively inexpensive to manufacture and convenient and safe to use. The present invention fulfills this need.

SUMMARY OF THE INVENTION

The present invention is embodied in an apparatus, and a related method, for use in the diagnostic analysis of a liquid specimen through binding assays. The apparatus includes a rigid body and a plurality of elongated strips, each coated with a binding assay component and supported on the body in spaced relationship for simultaneous contact with the liquid specimen. In accordance with the invention, the plurality of elongated strips are positioned across an elongated well formed in the rigid body, generally transverse to the well's longitudinal axis, and the apparatus further includes a cover plate secured to the rigid body and enclosing the elongated well. The strips are therefore protected during handling of the apparatus, and a specific volume of the liquid specimen can be confined and isolated in the well, where it can incubate with the strips. The apparatus is relatively inexpensive to manufacture and convenient and safe to use, particularly in applications using radioactive solutions.

More particularly, the apparatus of the invention is particularly suited for allergy screening, with each elongated strip being a cotton thread coated with a specific allergen. The rigid body preferably is formed of plastic and includes a flat land surrounding the elongated well. The threads are tensioned across the well, from the land on opposite sides of it, and the cover plate overlays the threads and is secured to the land.

To facilitate insertion of various liquids into the well, including the liquid specimen to be tested, suitable washing solutions, and a labeled antibody solution, the rigid body includes a port at each end of the elongated well. The apparatus further includes a pipette projection in alignment with the port located at one end of the well.

The cover plate preferably includes a thin plastic sheet in direct contact with the land of the rigid body, and an overlaying thin metallic sheet having a series of parallel narrow apertures, each aligned with a separate one of the cotton threads. The metal sheet enhances the measuring of the reaction of each cotton thread by reducing the interfering effects of adjacent threads. The plastic sheet is preferably secured to the land of the rigid body by a sonic weld, and the plastic sheet and metallic sheet are preferably secured to each other by an adhesive.

Other aspects and advantages of the present invention should become apparent from the following description of the preferred embodiment, taken in conjunction with the accompanying drawings, which illustrate, by way of example, the principles of the invention.

BRIEF DESCRIPTION OF THE DRAWINGS

FIG. 1 is a perspective view of an apparatus embodying the present invention, for use in the diagnostic analysis of a liquid specimen through binding assays, with a portion of the apparatus being cut away to reveal several allergen-coated threads disposed across an enclosed well;

FIG. 2 is a side sectional view of the apparatus, taken in the direction of the arrows 2—2 in FIG. 1;

FIG. 3 is a detailed sectional view of the apparatus, taken in the region indicated by the loop 3 in FIG. 2;

FIG. 4 is an exploded perspective view of the apparatus; and

FIG. 5 is an exploded sectional view of the apparatus, taken in the direction of the arrows 5—5 in FIG. 4.

DESCRIPTION OF THE PREFERRED EMBODIMENT

Referring now to the drawings, there is shown an apparatus for particular use in the immunoassay of a liquid specimen, such as blood serum, for simultaneously measuring the immune reaction to a plurality of antigens or allergens. The apparatus includes a plurality of threads 11 mounted in spaced relationship on a rigid body 13, each of the threads being coated with a different allergen or group of allergens. The threads are preferably formed of cotton, a high molecular weight polysaccharide, to permit allergen binding through cyanogen halide induced linkages, and are preferably spaced about 0.150 inches apart. In use, the coated threads are incubated with a specific amount of the liquid specimen to be tested, whereupon any specific IgE antibodies present in the specimen react with the corresponding allergens coated on the threads. Each allergen/IgE antibody conjugate is then detected using an anti-IgE antibody that is suitably labeled, preferably with a radioactive tracer such as $^{125}$I.

In accordance with the invention, the rigid body 13 includes an elongated well 15 and the coated threads 11 are positioned across the well, generally perpendicular to its longitudinal axis, and the apparatus further includes a cover plate 17 secured to the body and enclosing the well. Since the well is enclosed, the coated threads can be incubated with a specific volume of serum. The cover plate also protects the coated threads during handling, which otherwise might have an indeterminate effect on the immunoassay being conducted. In addition, the apparatus is relatively safe to use with radioactively-tagged anti-IgE antibodies, since after incubation with the radioactive solution, the radioactive threads are isolated during handling.

Prior to placement on the rigid body 13, the cotton threads 11 are activated using cyanogen bromide and then covalently bonded with prescribed allergens. One suitable technique for accomplishing this activation and coating is disclosed in the previously-identified U.S. Pat. No. 4,549,360.

The rigid body 13 is preferably injection molded of a plastic material such as polystyrene. The body includes a top port 19 and a bottom port 21 at opposite ends, in fluid communication with the well 15, for use in placing the various liquids in the well. The body is preferably formed with a top projection 23 in alignment with the top port and a bottom projection 25 in alignment with the bottom port. The top projection includes an annular flange 27 for locking engagement with the luer lock of a conventional syringe (not shown), and the bottom projection is appropriately tapered to accomodate a conventional removable pipette tip (not shown).

Liquids can be drawn into the well 15 through the pipette projection 25 and the bottom port 21 or can be flushed through the well, from the top port 19 to the bottom port. As shown in FIG. 4, the portion of the well adjacent the bottom port has a tapered segment 29 to facilitate a complete draining of the various liquids. The rigid body can further include a plurality of small tabs (not shown) projecting into the well, to disrupt the flow of any fluid being flushed through it and thereby create turbulence that enhances the washing of the coated threads 11.

The cover plate 17 preferably includes a thin plastic underlayer 31 and a thin metallic overlayer 33. The plastic underlayer is secured directly to a land 35 formed in the rigid body 13, surrounding the elongated well 15, and the metallic overlayer overlays the plastic underlayer and has a plurality of narrow apertures 37, each in alignment with a separate cotton thread 11. The apertures are uniformly spaced about 0.150 inches apart and each has a width of about 0.03 inches. In the preferred embodiment, the plastic underlayer is transparent and formed of a plastic such as polystyrene, in a thickness of about 5 mils, and the metallic overlayer is formed of a material such as copper, in a thickness of about 6 mils. The copper is plated with tin, to prevent any reaction occuring between the copper and an azide in a conventional phosphate buffered saline carried in the well 15 prior to use.

The plastic underlayer 31 is secured to the metallic overlayer using an adhesive such as a UV-activated adhesive available from Loctit Co. of San Jose, Calif. This adhesive can be sprayed onto the underside of the metallic layer. The plastic layer is, in turn, secured to the land 35 of the rigid body 13 by a sonic weld. The body further includes an embossment 39 in the land, encircling the well 15 approximately midway between the inner periphery and the outer periphery of the land. As shown in FIG. 5, the embossment has a triangular cross-section and functions to direct the energy of the sonic weld.

The sonic welding process also serves to hold the cotton threads 11 in their prescribed, spaced positions. Prior to welding, each thread is placed under tension, to ensure that it will be stretched tautly across the well 15. After welding, any portions of the threads projecting beyond the edges of the rigid body 13 are removed.

The metallic overlayer 33 ensures that the relatively close spacing of the cotton threads 11 will not preclude an accurate measurement of the reaction on each thread. Each aperture 37 in the overlayer transmits the radiation emitted by the corresponding thread only in a relatively narrow beamwidth, ensuring that radiation emitted by neighboring threads will not interfere with the measurement. This shielding is effective for a variety of measurement techniques, including techniques using a gamma counter or photographic film. A thickness of 6 mils for the metallic overlayer is preferred because it is believed to be the minimum thickness required to prevent an undesired amount of interference with adjacent thread measurements.

As shown in FIG. 5, the rigid body 13 further includes an elongated recess 41 on its underside, i.e., the side opposite from that of the well 15. This recess provides the body with improved rigidity.

In use, the rigid body 13 is oriented in a generally vertical position, with the pipette projection 25 facing downwardly. The liquid specimen to be tested can be drawn into the well 15 through the pipette projection and bottom port 21 using a suitable syringe (not shown) coupled to the top projection 23. The specimen is drawn into the well such that all of the cotton threads 11 are immersed, about 1.2 to 1.3 ml of liquid being required in the preferred embodiment, and the threads are then incubated for a prescribed time duration. The particular time duration prescribed depends on the allergen concentrations of the coated threads. One set of suitable concentrations and incubation time durations is disclosed in the aforementioned U.S. Pat. No. 4,459,360. Care should be taken to avoid agitation of the liquid during incubation. After incubation, any IgE antibodies present in the specimen will have reacted with the corresponding allergens coated on the various threads.

After the liquid specimen has incubated with the coated threads 11 for the prescribed duration, it is drained from the well 15 through the bottom port 21 and the threads are washed with a phosphate buffered saline. This washing reduces non-specific binding of antibodies to the coated threads. A suitable radioactively-labeled anti-IgE antibody solution is then drawn into the well through the bottom port. After incubation for a prescribed time duration, a substantial proportion of the allergen/IgE antibody conjugates present on the threads will have reacted with the anti-IgE antibodies. The labeled antibody solution is then drained from the well through the bottom port.

After again flushing the well 15 with a phosphate buffered saline, the apparatus is in condition for measurement of the various reactions that might have occurred. The number of labeled anti-IgE antibodies bonded to each cotton thread 11 indicates the degree of the allergic reaction to the corresponding allergen.

When a radioactive label such as $^{125}I$ is used, the reaction for each coated thread 11 can be measured using a gamma counter or by exposing a suitable photographic film. In the latter case, sensitivity of the measurement can be enhanced by using a suitable phosphor for converting the radioactive emissions to a wavelength more suitable for the photographic film. The phosphor can be in the form of a screen located adjacent to the film or in some other form juxtaposed with the thread. The exposure time depends, of course, on the range of radioactivity to be measured, the sensitivity of the film, and the film temperature.

It should be appreciated from the foregoing description that the present invention provides an improved apparatus for particular use in the immunoassay of a liquid specimen by simultaneously measuring the immune reaction of the specimen to a plurality of antigens or allergens. The apparatus includes a plurality of elongated strips, preferably in the form of cotton threads, each thread being coated with a different allergen or group of allergens. The threads are disposed within an enclosed well of prescribed volume, thereby enhancing the accuracy of the immunoassay and ensuring that the apparatus can be safely handled when used with a radioactively-labeled antibody as a part of a radioimmunoassay test.

Although the invention has been described in detail with reference to the presently-preferred embodiment, it should be understood by those of ordinary skill in the art that various modifications can be made without departing from the invention. Accordingly, the ivnention is limited only by the following claims.

We claim:

1. For use in a system for the diagnostic analysis of a liquid specimen through binding assays, an apparatus comprising:
   a rigid body having an elongated well therein for receiving a liquid specimen;
   a plurality of elongated strips oriented in spaced relationship to each other across the elongated well and generally transverse to its longitudinal axis and disposed for contacting the liquid specimen, each strip being coated with a binding assay component such that reactive components in the liquid specimen will be bound thereto; and
   a cover plate connected to the rigid body and enclosing the elongated well.

2. An apparatus as defined in claim 1, wherein the plurality of elongated strips are cotton threads.

3. An apparatus as defined in claim 1, wherein:
   the rigid body includes a substantially flat land surrounding the elongated well; and
   the cover plate is substantially flat and is secured to the land of the rigid body, to enclose the elongated well.

4. An apparatus as defined in claim 3, wherein the cover plate includes a thin metallic sheet having a plurality of elongated apertures aligned with each of the plurality of elongated strips.

5. An apparatus as defined in claim 4, wherein the cover plate further includes a thin plastic sheet disposed between the rigid body and the thin metallic sheet.

6. An apparatus as defined in claim 5, wherein:
   the rigid body is formed of a plastic material;
   the plastic sheet and the metallic sheet are secured to each other by an adhesive; and
   the plastic sheet is secured to the land of the rigid body by a sonic weld.

7. An apparatus as defined in claim 5, wherein the thin plastic sheet is transparent.

8. An apparatus as defined in claim 3, wherein each of the elongated strips extends across the well from the land on opposite sides of the well.

9. An apparatus as defined in claim 1, wherein the plurality of elongated strips are held in tension across the elongated well and are each substantially straight and parallel with each other.

10. An apparatus as defined in claim 1, wherein the rigid body further includes a port at each end thereof and communicating with the well, so that the liquid specimen may be inserted into the well through a port.

11. An apparatus as defined in claim 10, wherein the rigid body further includes a pipette projection in alignment with the port located at one end of the elongated well.

12. Apparatus for use in a system for the allergy screening of a liquid specimen through binding assays, the apparatus comprising:
   a rigid plastic body having an elongated, shallow well formed therein, and a substantially flat land surrounding the well;
   a plurality of cotton threads stretched tautly across the elongated well from the land on its opposite sides, the threads being oriented in spaced parallel relationship substantially perpendicular to the longitudinal axis of the elongated well and disposed for contacting the liquid specimen, each thread coated with a different allergen or group of allergens for binding corresponding antibodies in the liquid specimen;
   a substantially flat cover plate secured to the land of the rigid body, to enclose the elongated well, the cover plate including
      a thin, transparent plastic sheet overlaying to the land of the rigid body, and
      a thin metallic sheet overlaying the plastic sheet and having a plurality of elongated apertures aligned with each of the plurality of cotton threads; and
   means defining a port at each end of the elongated elongated well, to facilitate insertion and removal of a liquid specimen in the well, for contact with the plurality of cotton threads.

13. A method for the diagnostic analysis of a liquid specimen through binding assays, comprising the steps of:

coating each of a plurality of elongated strips with a binding assay component such that reactive components in the liquid specimen will be bound thereto;

positioning the plurality of elongated strips in a predetermined spaced relationship to each other in a chamber of prescribed volume formed within a rigid body;

placing a liquid specimen in the chamber and incubating the specimen in contact with the coated strips;

removing the liquid sample from the chamber; and measuring the reaction occurring between the liquid specimen and each of the coated strips.

14. A method as defined in claim 13 wherein:

the chamber is defined by an elongated, shallow well formed in the rigid body;

the step of positioning includes a step of stretching the elongated strips across the well, generally transverse to its longitudinal axis; and the method further includes a step of securing a cover plate to the rigid body, to enclose the well and thereby form the chamber.

15. A method as defined in claim 14, wherein the step of securing sonically welds the cover plate to the rigid body.

16. A method as defined in claim 14, wherein said cover plate includes on its outside surface a thin metallic sheet having a plurality of elongated apertures therethrough in alignment with each of the plurality of elongated strips.

17. A method as defined in claim 13, wherein the plurality of elongated strips positioned in the step of positioning are cotton threads.

* * * * *